United States Patent [19]

Yokoi et al.

[11] Patent Number: 4,501,752
[45] Date of Patent: Feb. 26, 1985

[54] ANTIULCER DRUG

[75] Inventors: Koichi Yokoi, Kashiwa; Koichi Tachibana, Narita; Kazuo Isomae, Narashino; Toshiaki Nakashima, Shisuimachi, all of Japan

[73] Assignee: SS Pharmaceutical Co., Ltd., Tokyo, Japan

[21] Appl. No.: 487,829

[22] Filed: Apr. 22, 1983

[30] Foreign Application Priority Data

Apr. 30, 1982 [JP] Japan .................................. 57/72960

[51] Int. Cl.³ .......................................... A61K 31/395
[52] U.S. Cl. .............................. 514/414; 260/239.3 P
[58] Field of Search .................. 260/239.3 P; 424/274

[56] References Cited

PUBLICATIONS

Ito et al., "Bull. Chem. Soc. Japan", vol. 50, No. 7, pp. 1813–1820, (1977).

Primary Examiner—Robert T. Bond
Attorney, Agent, or Firm—Oblon, Fisher, Spivak, McClelland & Maier

[57] ABSTRACT

An antiulcer drug comprising Ikarugamycin as its active ingredient is disclosed.

16 Claims, No Drawings

ANTIULCER DRUG

BACKGROUND OF THE INVENTION

This invention relates to a novel antiulcer drug comprising Ikarugamycin as its active ingredient. Ikarugamycin is a compound whose pharmacological action has not yet been known at all except that it has been known merely as an antibiotic having a trichomonacidal effect and showing a weak antibacterial effect against gram positive bacteria.

The present inventors have made an intensive study on the pharmacological activity of Ikarugamycin and accomplished the present invention based on the finding that the compound exhibits an excellent antiulcer activity.

SUMMARY OF THE INVENTION

Accordingly, an object of the present invention is to provide an antiulcer drug comprising as its active ingredient Ikarugamycin represented by the following formula (I):

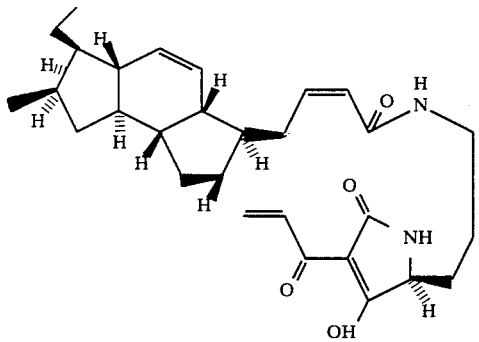

DETAILED DESCRIPTION OF THE INVENTION AND PREFERRED EMBODIMENTS

Ikarugamycin used in the present invention is an acidic compound in the form of fine needles having a molecular formula of $C_{29}H_{38}N_2O_4$ with a molecular weight of 478, melting point of 252°–255° C., soluble in various types of organic solvents and insoluble in water. It can be easily produced by the fermentation method disclosed, for example, in Japanese Patent Publication No. 28833/1971.

The structural formula of Ikarugamycin is the following:

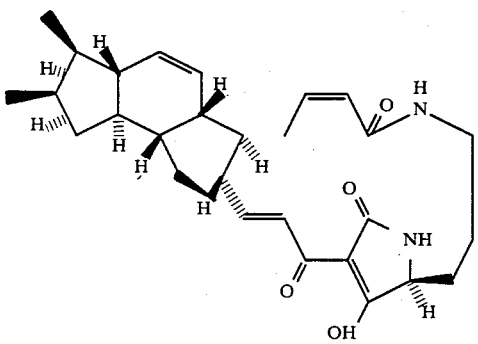

Antiulcer effects of Ikarugamycin are shown below.

(1) Effect Against Indomethacin-induced Ulcer

Several groups of 7 weeks old male Donryu rats, each weighing 180–200 g and each group consisting of 6 rats were provided and fasted over 48 hours, after which a specimen prepared by dissolving Ikarugamycin into saline incorporated with 5% dimethylsulfoxide was orally administered by a predetermined amount to each rat.

One hour later, Indomethacin was orally administered by 25 mg/kg and, 5 hours later, 2% Brilliant blue solution was intravenously injected to them and their stomachs were extracted. The stomachs were cut and opened to measure the major diameters of the ulcerated portions. The sum of the lengths (mm) was taken as an ulcer index.

The results are shown in Table 1.

TABLE 1

| Dose of Ikarugamycin (mg/kg) | Ulcer Index (mean value ± Standard error) | Ulcer Inhibition Rate (%) |
|---|---|---|
| 0.03 | 17.3 ± 4.0 | 30 |
| 0.3 | 10.0 ± 1.6 | 60 |
| 1.0 | 9.0 ± 1.9 | 64 |
| 3.0 | 6.7 ± 1.6 | 73 |
| 10.0 | 3.1 ± 1.0 | 87 |
| 30.0 | 2.8 ± 1.1 | 89 |
| Control Group | 24.7 ± 4.2 | — |

(2) Effect Against Stress-induced Ulcer

Several groups of 7 weeks old male Donryu rats, each weighing 180–200 g and each group consisting of 6 rats were used. Specimen prepared by dissolving Ikarugamycin into saline incorporated with 5% dimethylsulfoxide was orally administered by a predetermined amount to each rat. The rats were held vertically and immersed neck-high in a bath of 23° C. water for 24 hours. Thereafter, 2% Brilliant blue solution was intravenously injected to them and their stomachs were extracted to determine the ulcer index, which was obtained from the same procedures as in (1) shown above.

The results are shown in Table 2.

TABLE 2

| Dose of Ikarugamycin (mg/kg) | Ulcer Index (mean value ± Standard error) | Ulcer Inhibition Rate (%) |
|---|---|---|
| 3.0 | 5.1 ± 2.0 | 77 |
| 10.0 | 3.4 ± 2.2 | 85 |
| Control Group | 22.2 ± 2.1 | — |

As mentioned in the above, Ikarugamycin shows an excellent inhibitive effect against the experimental ulcer. Moreover, the 50% mortality ($LD_{50}$) of Ikarugamycin is higher than 1000 mg/kg (mouse, oral dose), which shows enough harmlessness of the drug.

The manner and the amount for administering the antiulcer drug according to this invention are shown below.

The administration is preferably carried out orally in the form of, for example, tablets, capsules, granules, syrups and the likes.

The amount of administration is suitably in the range of 0.01–500 mg/kg daily in one to several divided oral doses for adults.

Formulations for the oral administration can be made by a usual manner of manufacture. That is, tablets, capsules, granules or the likes can be produced by formulating the compound in combination with excipients such as starch, lactose, mannitol and the like; binders such as carboxymethyl cellulose sodium, hydroxypropyl cellulose and the like; disintegrators such as crystalline cellulose, carboxymethyl cellulose calcium and the like; emollients such as talc, magnesium stearate and the like; and fluidity improvers such as light anhydrous silicic acid and the like.

The antiulcer drug according to the present invention will now be explained by way of the following examples.

EXAMPLE 1. Tablet

One tablet of the following formulation was prepared according to a usual manner.

| Ikarugamycin | 100 mg |
| --- | --- |
| D-mannitol | 150 |
| Crystalline cellulose | 50 |
| Starch | 28 |
| Carboxymethyl cellulose calcium | 16 |
| Talc | 4 |
| Magnesium stearate | 2 |
| Total | 350 mg |

EXAMPLE 2. Capsule

Granules of the following formulation were prepared by a usual manner, and were charged in a No. 3 capsule.

| Ikarugamycin | 25 mg |
| --- | --- |
| Crystalline cellulose | 17 mg |
| Light anhydrous silicic acid | 7 mg |
| Magnesium stearate | 1 mg |

What is claimed is:

1. An antiulcer drug comprising:
    (a) an antiulcer effective amount of Ikarugamycin of the following formula:

(b) a pharmaceutical acceptable excipient.

2. A method for treating or preventing ulcers which comprises administering to animals or humans in need of said treatment an effective amount of Ikarugamycin.

3. The antiulcer drug of claim 1 in a form suitable for oral administration.

4. The antiulcer drug of claim 3, in the form of a tablet, capsule, granules or syrup.

5. The antiulcer drug of claim 1, wherein the excipient is selected from the group consisting of starch, lactose, and mannitol.

6. The antiulcer drug of claim 1, further comprising a binder.

7. The antiulcer drug of claim 6, wherein the binder is selected from the group consisting of carboxymethyl cellulose sodium and hydroxypropyl cellulose.

8. The antiulcer drug of claim 1 further comprising a desintegrator.

9. The antiulcer drug of claim 8, wherein the desintegrator is selected from the group consisting of crystalline cellulose and carboxymethyl cellulose.

10. The antiulcer drug of claim 1 further comprising an emollient.

11. The antiulcer drug of claim 10, wherein the emollient is selected from the group consisting of talc, and magnesium stearate.

12. The antiulcer drug of claim 1 further comprising a fluidity improving substrate.

13. The antiulcer drug of claim 12, wherein the fluidity improving substrate is light anhydrous silicic acid.

14. The antiulcer drug of claim 1 in unit dosage form.

15. The antiulcer drug of claim 14, wherein Ikarugamycin is present in an amount between 0.01–500 mg/kg.

16. The method for treating or preventing ulcers of claim 2, wherein Ikarugamycin is administered in an amount of 0.01–500 mg/kg daily.

* * * * *